Figure 1:
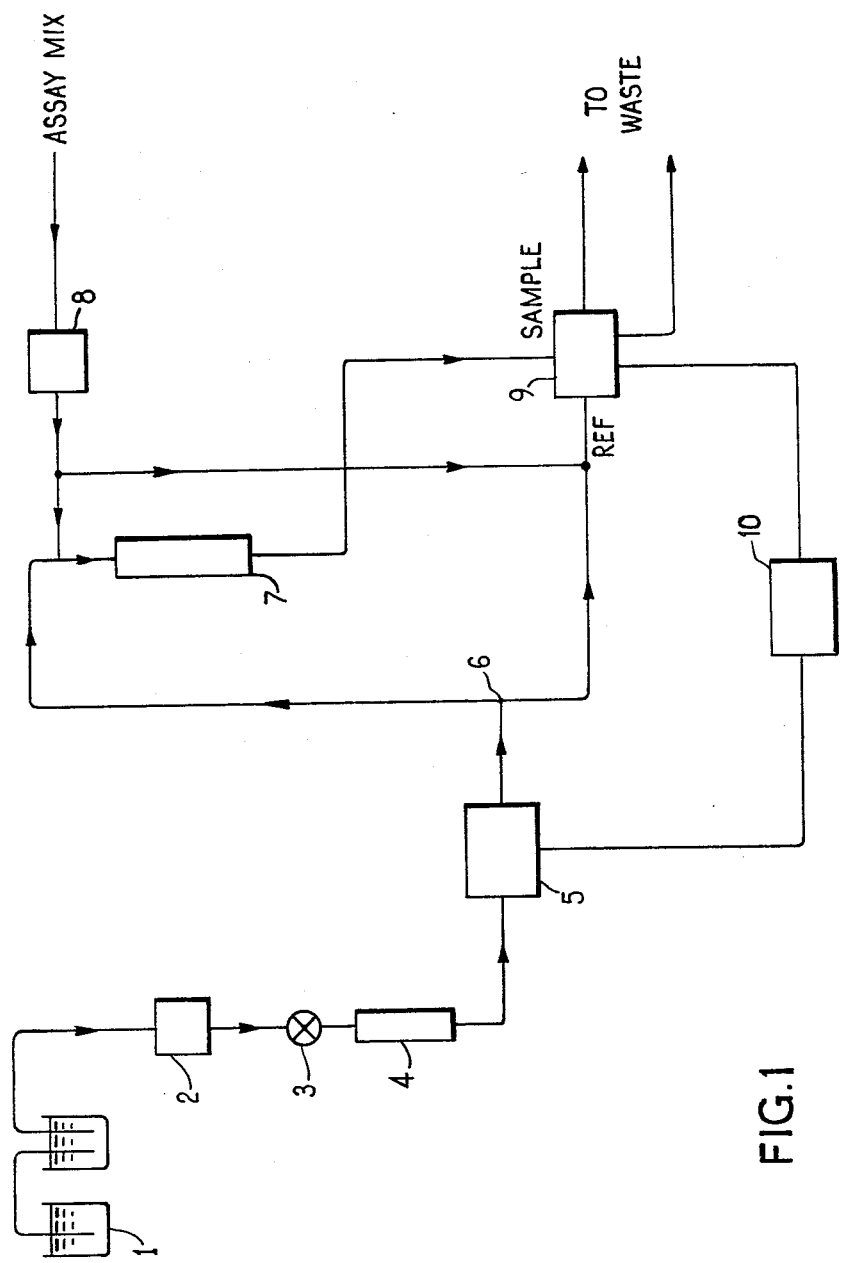

United States Patent [19]

Atkinson et al.

[11] 4,431,544
[45] Feb. 14, 1984

[54] HIGH PRESSURE LIQUID AFFINITY CHROMATOGRAPHY

[75] Inventors: Anthony Atkinson, Salisbury; Christopher R. Lowe, Eastleigh, all of England; Klaus Mosbach, Lund, Sweden; David A. P. Small, Winterslow, England

[73] Assignee: The Public Health Laboratory Service Board, London, England

[21] Appl. No.: 372,020

[22] Filed: Apr. 26, 1982

[30] Foreign Application Priority Data

Apr. 27, 1981 [GB] United Kingdom ............ 8112897

[51] Int. Cl.³ ............................................. B01D 15/08
[52] U.S. Cl. .................................. 210/635; 210/656; 210/198.2; 210/502.1
[58] Field of Search ............... 210/635, 656, 198.2, 210/502; 435/815

[56] References Cited

U.S. PATENT DOCUMENTS

| | | | |
|---|---|---|---|
| 4,016,149 | 4/1977 | Travis et al. | 210/635 X |
| 4,118,316 | 10/1973 | Talley et al. | 210/502 X |
| 4,336,161 | 6/1982 | Rosewear et al | 210/656 X |

OTHER PUBLICATIONS

Chromatographic and Allied Methods by Mikes, John Wiley & Sons, New York, pp. 388–391 and 407–410.
Methods in Enzymology, vol. XLV by Lorand, pp. 462–466.
P.D.G. Dean et al, J. Chromatogr., 1979, 165, 301.
D.A.P. Small et al, J. Chromatogr. 1981, 216, 175.
C. R. Lowe et al, J. Chromatogr., 1981, 215, 303.

*Primary Examiner*—John Adee
*Attorney, Agent, or Firm*—Cushman, Darby & Cushman

[57] ABSTRACT

A process for the high pressure liquid affinity chromatographic separation of at least one biological or related substance from a mixture in which the contact, washing and eluting phases are performed on a binding material made from a ligand, containing at least one of the groups anthraquinone, phthalocyanine or aromatic azo, coupled to a matrix through a spacer arm, the binding material being so constructed that at least one biological or related substance is retained on the binding material during the contact and washing phases. In one preferred embodiment the ligand is a reactive dye, especially a triazinyl dye, the matrix is agarose or silica and the spacer arm is a substituted aminohexyl group. The chromatographic procedure is preferably performed at 100–3500 psi, at a flow rate of 0.5–2.0 ml/min. The choice of washing and eluting solutions depends on the material to be separated. However buffer solution to wash the column and a desorbing agent to elute the material are preferred. When the biological substance is an enzyme the desorbing agent is preferably an enzyme substrate, cofactor, inhibitor or analogue thereof. A binding material for use in the above HPLAC procedure is also provided. This is made from a ligand containing at least one of the groups anthraquinone, phthalocyanine or aromatic azo, coupled to a matrix through a spacer arm.

13 Claims, 2 Drawing Figures

HIGH PRESSURE LIQUID AFFINITY CHROMATOGRAPHY

The present invention relates to a process for the high pressure liquid chromatographic separation of biological or related substances and to a biological or related substance binding material for use in the said process.

High pressure (or performance) liquid chromatography (HPLC) is a development of liquid chromatography techniques in which the liquid mobile phase is forced, under pressure, through the stationary phase.

HPLC has a number of advantages over other forms of liquid chromatography, for example:

a. Separation of mixtures can be performed more quickly.
b. Resolution of mixtures far exceeds that of older methods.
c. Technique is less dependent on the operator's skill and reproducibility is greatly improved, and
d. Instrumentation of HPLC lends itself to automation and quantitation.

Affinity chromatography is a well known technique for the separation of biological or related molecules which employs the biospecific interactions between the molecule being isolated and another molecule (ligand) immobilised on a stationary support (matrix). The ligand must interact specifically and reversibly with the molecule to be separated. It is generally immobilised on the support by reacting a ligand precursor with the matrix.

A typical affinity chromatographic process comprises:

a. The contact phase, wherein a mixture containing the desired biological or related substance is contacted with a binding material, retained on a chromatographic column and, comprising a ligand attached to a matrix.
b. The washing phase, wherein the non-binding species are removed from the binding material by passing a washing solution therethrough, and
c. The elution phase, wherein an eluting solution is passed through the binding material to recover the desired biological or related substance from the column.

By the careful choice of the binding material, washing solution and eluting solution a one-step purification of complex mixtures of biological or related substances can be achieved.

It is the aim of the present invention to provide a high pressure (performance) liquid affinity chromatographic process which combines the affinity chromatographic and HPLC techniques outlined above. In this hybrid HPLAC technique the contact, washing and, optionally, elution phases are performed under a high pressure of liquid. In particular it is the aim of the present invention to provide an HPLAC process which employs ligands derived from, reactive dyes, especially anthraquinones, phthalocyanines or aromatic azo compounds, bound indirectly to suitable matrices, especially metal oxide or cross-linked matrices, and which allows the efficient separation of biological substances, especially proteins, from mixtures containing same.

According to the present invention there is provided a process for the high pressure liquid affinity chromatographic separation of at least one biological or related substance from a mixture wherein contact, washing and elution phases are performed on a binding material comprising a ligand, containing at least one of the groups anthraquinone, phthalocyanine or aromatic azo, coupled to a matrix through a spacer arm said binding material being so constructed that the at least one biological or related substance is retained on the binding material during the contact and washing phases.

The biological or related substance may be any material that binds specifically to the ligands employed in the process of the present invention, for example peptides, polypeptides, proteins, nucleotides, polynucleotides, nucleic acids, steroids, lipids, hormones. Generally however the biological or related substance will be an enzyme, protein or polypeptide, for example albumin, peptidases phosphatases, kinases, such as glycerokinase, hexokinase or urokinase, nucleases, such as restriction endonucleases or ribonuclease, dehydrogenases, such as glyceraldehyde-3-phosphate dehydrogenase lactate dehydrogenase, liver alcohol dehydrogenase or glucose-6-phosphate dehydrogenase, esterases, synthetases, DNA or RNA binding proteins.

The ligand is any material containing an anthraquinone, preferably a sulphonated anthraquinone, phthalocyanine or aromatic azo group which interacts with the biological or related substance to be separated both specifically and reversibly.

The ligands of the present invention preferably are derived from ligand precursors commonly known as reactive dyes. These dyes include pyrazinyl, pyrimidinyl, pyridazinyl or sulphone derivatives of an anthraquinone (I) or an aromatic azo group (II).

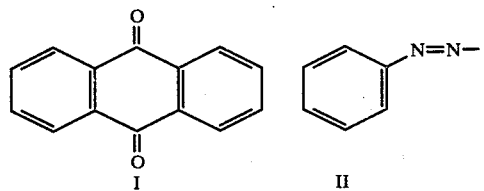

For example, dyes sold under the trade marks Reactone (J. R. Geigy SA), Drimarene (Sandoz Ltd), Levafix (Farbenfabriken Bayer AG), Cavalite (Du Pont de Nemours Inc), Remazol (Farbwerke Hoechst AG), and Primazin (Badische Anilin u.Soda Fabrik A.G.).

Preferably however the dyes are triazinyl derivatives of anthraquinones, phthalocyanines or aromatic azo compounds. Such compounds have the general structure III

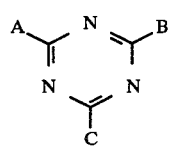

wherein A is an organic substituent containing an anthraquinone, preferably a sulphonated anthraquinone, an aromatic azo or a phthalocyanine group; B is an organic substituent, preferably a sulphonated aromatic group, a halogen atom, preferably a chlorine atom, or an amino or substituted amino group; and C is a leaving group, preferably a chlorine atom, which is displaced in a nucleophilic substitution reaction.

These preferred reactive dyes are commonly known as "triazinyl dyes". Examples of this type of dye that are particularly suitable for use in the separation of biological or related substances by the process of the present invention include those sold under the trade marks Cibacron (Ciba Ltd) and Procion (ICI) for example:
Cibacron Orange G-E, Cibacron Brilliant Blue FBR-P, Cibacron Blue F3G-A, Cibacron Brilliant Red 3B-A, Cibacron Brown 3 GR-A, Cibacron Scarlet 2G, Cibacron Scarlet 4G-P,
Cibacron Brilliant Red B-A, Procion Brilliant Orange HGRS,
Procion Blue HBS, Procion Brilliant Red H7BS, Procion Orange
Brown HGS, Procion Scarlet H3GS, Procion Red H3B, Procion Red HE3B,
Procion Red P3BN, Procion Red MX2B, Procion Blue MX3G,
Procion Yellow MXR, Procion Yellow H5G, Procion Red H8BN,
Procion Green H-4G, Procion Brown MX5BR, Procion Blue MX-G,
Procion Blue HE-RD, Procion Blue H-B, Procion Blue MXR,
Procion Yellow HA and Procion Green HE-4BD.

When commercial dyes are used it may be necessary to remove wetting agents, by, for example, washing with an organic solvent, for example ether or acetone.

The matrix is any support commonly used for affinity chromatography media which is compatible with (that is, will function as an affinity chromatography support at) HPLAC operating pressures. Thus polyamino-, polyamido- or polyhydroxylic matrices may be used, including polysaccharides, such as cross-linked cellulose, agarose, dextrose and dextran, cross-linked polyamides such as polyacrylamide, and copolymers of these materials, such as cross-linked polyacrylamide-agarose gells. Alternatively, metal oxides, such as alumina, titania, zirconia or, especially, silica, or glass beads may be used.

The spacer arm may have any structure that, when combined with the matrix and the ligand, ensures that the biological substance to be separated is retained on the binding material during the contact and washing phases of HPLAC.

Generally the spacer arm, shown below in its position in the binding material IV between the matrix and the ligand, has the structure X-R-Y Matrix—X—R—Y—Ligand (IV)

Its position in a preferred binding material is shown in general formula V

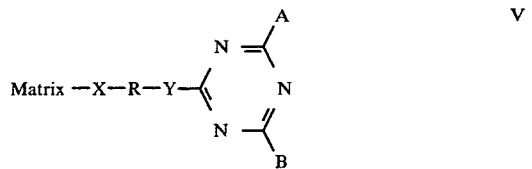

X is an organic or organometallic functional group, bound directly to the matrix, and having a structure which varies with the choice of matrix. For example, when the matrix is a polysaccharide, particularly cross-linked agarose, X may comprise one or more of the following groups, an alkyl, a substituted alkyl, especially an alkylalcohol, a diol, a carboxylate, an ether, a thioether, an amido, an amino, an amidino, an imino carboxylate, an isourea, a carbamate or a guanidino group. These groups may be in monomeric, oligomeric or polymeric form. When the matrix is polyacrylamide, X maybe a carboxy group, either alone or attached to an organic group. When the matrix is silica, X may be

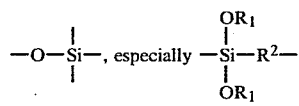

wherein $R_1$ is H or alkyl, $R^2$ is an organic group which may comprise one or more of the following groups, an alkyl, a substituted alkyl, especially an alkylalcohol, a diol, an ether, an amido or an amino group, and optionally one or more of the following groups, an epoxy, a carboxylate, a thioether, an amidino, an imino carboxylate, an isourea, a carbamate or a guanidino group. Again these groups may be in monomeric, oligomeric or polymeric form. In particularly preferred embodiments of this invention $R^2$ is one or more of alkyl, substituted alkyl and alkyl ether.

Y is a nucleophilic group or atom directly bound to the ligand. In the preferred ligands of the present invention Y is directly bound to the diazinyl or triazinyl ring. Y may be, for example, an alkyl, an ether, a thioether, an amido or an amino group or, which is preferred, it may be —NH—, —O— or —S—.

R is an organic group and may comprise one or more of the following groups an alkyl, an alkene, an α-aminoalkyl, an α-oxyalkyl, an α-thioalkyl, an alkylalcohol, a diol, a carboxylate, an ether, a thioether, an amido, an amino, an amidino, an imino carboxylate, an isourea, a carbamate, a guanidino, a hydrazino, an aromatic or a heterocyclic group. These groups may be in monomeric, oligomeric or polymeric form. Particularly preferred groups include —CH$_2$—$_n$, —NH—CH$_{2n}$, —O—CH$_2$—$_n$ and —S—CH$_2$—$_n$, wherein n is from 1 to 12. Other preferred groups include polyethyleneimine, polyaminoacids, such as polylysine or polyarginine, polyvinylpyrrolidone, polyornithine, polyvinylamine or phenyl derivatives.

The spacer arm may be produced between the matrix and the ligand by any of the following, non-exhaustive list of procedures:
a. Modifying the matrix and reacting the ligand precursor with the modified matrix,
b. Modifying the ligand precursor and reacting the modified ligand precursor with the matrix,
c. Modifying both the matrix and the ligand precursor and then reacting both modified substances together, or
d. Modifying the matrix and then reacting the modified matrix with the unmodified ligand precursor.

Examples of method a. include reacting cross-linked agarose consecutively with cyanogen bromide and an α, w-diaminoalkane to give an aminoalkyl isourea derivative followed by reaction of this modified matrix with a 2, 4 or 6 mono or dichloro triazinyl containing ligand precursor to afford the binding material. Alternatively silica may be reacted consecutively with w-glycidoxyalkyltrialkoxy silane and α,w-aminoalkyl substituted silica and this modified matrix may be reacted with a 2, 4 or 6-mono or dichlorotriazinyl containing ligand precursor to afford the binding material. In an alternative embodiment the silica may be reacted consecutively with w-thioalkyltrialkoxysilane and a mono or dichlorotriazinyl ligand precursor to afford a sulphur containing binding material.

Examples of method b. including reacting the mono or dichloro substituted ligand precursor with an α, w-diaminoalkane and then adding this modified ligand to cyanogen bromide activated cross-linked agarose to form the binding material.

Examples of method c. include reacting the mono or dichloro substituted ligand precursor with an α, w-diaminoalkane, separately reacting silica with w-glycidoxyalkyltrialkoxysilane and then adding the modified ligand precursor to the modified matrix to form the binding material.

Examples of method d. include reacting silica with w-glycidoxyalkyltrialkoxysilane under acidic conditions to form a diol and then reacting the modified matrix with a 2, 4 or 6-mono- or dichlorotriazinyl containing liquid precursor.

In one particularly preferred embodiment of the present HPLAC process the biological or related substance is bound to the binding material in the presence of metal ions, as described in our copending UK application no 8112925. Preferred metal ions are $Co^{2+}$, $Ni^{2+}$, and $Zn^{2+}$, with $Zn^{2+}$ being particularly preferred.

When metal ions are employed the contact solution (the solution that is passed through the binding material in the contact phase) generally comprises the mixture containing the biological or related substance and a salt of the metal ion, both dissolved in a buffer solution. Alternatively, in some cases, the contact solution may simply comprise the mixture in a buffer solution. In this latter embodiment, however, before the contact solution is passed through the chromatographic column, the binding material on said column must first be treated with a buffer solution containing the metal salt.

The conditions and methods employed in conventional high pressure liquid chromatography (HPLC) and affinity chromatography may be used in the process of the present invention. For example the process may be performed at any pressure between about 10 and 5000 psi, preferably between about 100 and 3500 psi. Generally all three affinity chromatographic phases (contact, washing and eluting) are performed under high pressure, but in one embodiment of the process of the present invention the eluting phase may be performed at atmospheric pressure.

The liquid flow rate through the binding material will depend on the pressure adopted, but is typically between about 0.1 and 3.0 ml/min, preferably 0.5 and 2 ml/min.

The binding material is generally retained on a chromatographic column of rigid construction, typically metal construction. The length and width of the column, together with the particle size of the binding material will generally be varied with the quantity of the biological substance to be separated. In order to scale up an HPLAC procedure according to this invention from an analytical to a preparative scale and to achieve the same degree of separation in the same time for the same pressure drop, the column and width together with the particle size of the binding material should be increased.

The nature of the washing and eluting solutions will depend on the biological substance to be separated. Generally the composition of these solutions will be the same as that conventionally used for similar systems in the affinity chromatography art. Thus the washing solution may be a buffer solution, for example potassium phosphate. The pH of the buffer solution will be chosen to ensure that the activity of the biological substance bound to the column is retained while the "non-complementary" (non-binding) constituents of the mixture are washed through the binding material.

The eluting solution, on the other hand, may contain a desorbing agent specific for the biological or related substance bound to the binding material. The desorbing agent may be, for example, a ligand presursor which is complementary to the biological substance bound to the column. Alternatively, when the biological substance is an enzyme the desorbing agent may be an enzyme substrate, cofactor, inhibitor or analogues thereof. Thus, in the case of lactate dehydrogenase (LDH) a preferred desorbing agent is its cofactor nicotinamide adenine dinucleotide (NAD) or a mixture of its cofactor NAD and its substrate pyruvate, while in the case of liver alcohol dehydrogenase (LADH) a preferred desorbing agent is its cofactor NAD in admixture with an inhibitor pyrazole. The choice of other desorbing agents specific for a given ligand-biological substance system will be apparent to those skilled in the affinity chromatography art.

It will be seen from the above that by careful choice of ligands and desorbing agents the separation of mixtures of two or more biological substances may be effected in one step by the process of the present invention. For example a mixture of LDH and LADH may be separated by the process of the present invention on an appropriately modified silica - Cibacron Blue F3G-A column by passing solutions of NAD/pyruvate and NAD/pyrazole consecutively through the column.

Once the biological substance has been eluted from the binding material it may be identified by an appropriate assay system. The choice of assay system for a particular biological substance is entirely conventional and will be immediately apparent to those skilled in this art.

In a further aspect of the present invention there is provided a binding material for use in the high pressure liquid affinity chromatographic (HPLAC) separation of at least one biological or related substance from a mixture comprising a ligand containing at least one of the groups anthraquinone, phthalocyanine or aromatic azo, coupled to a matrix through a spacer arm said binding material being so constructed that the at least one biological or related substance is retained on the binding material during the contact and washing phases of HPLAC.

The matrix and the spacer arm may be any of those preferred for use in the process of the present invention. The ligand is preferably derived from any of the "reactive dye" ligand precursors listed above especially the diazinyl or triazinyl dyes. The binding material is preferably prepared by the direct substitution of a leaving group on the ligand precursor by the matrix-spacer moiety.

Figure 2:
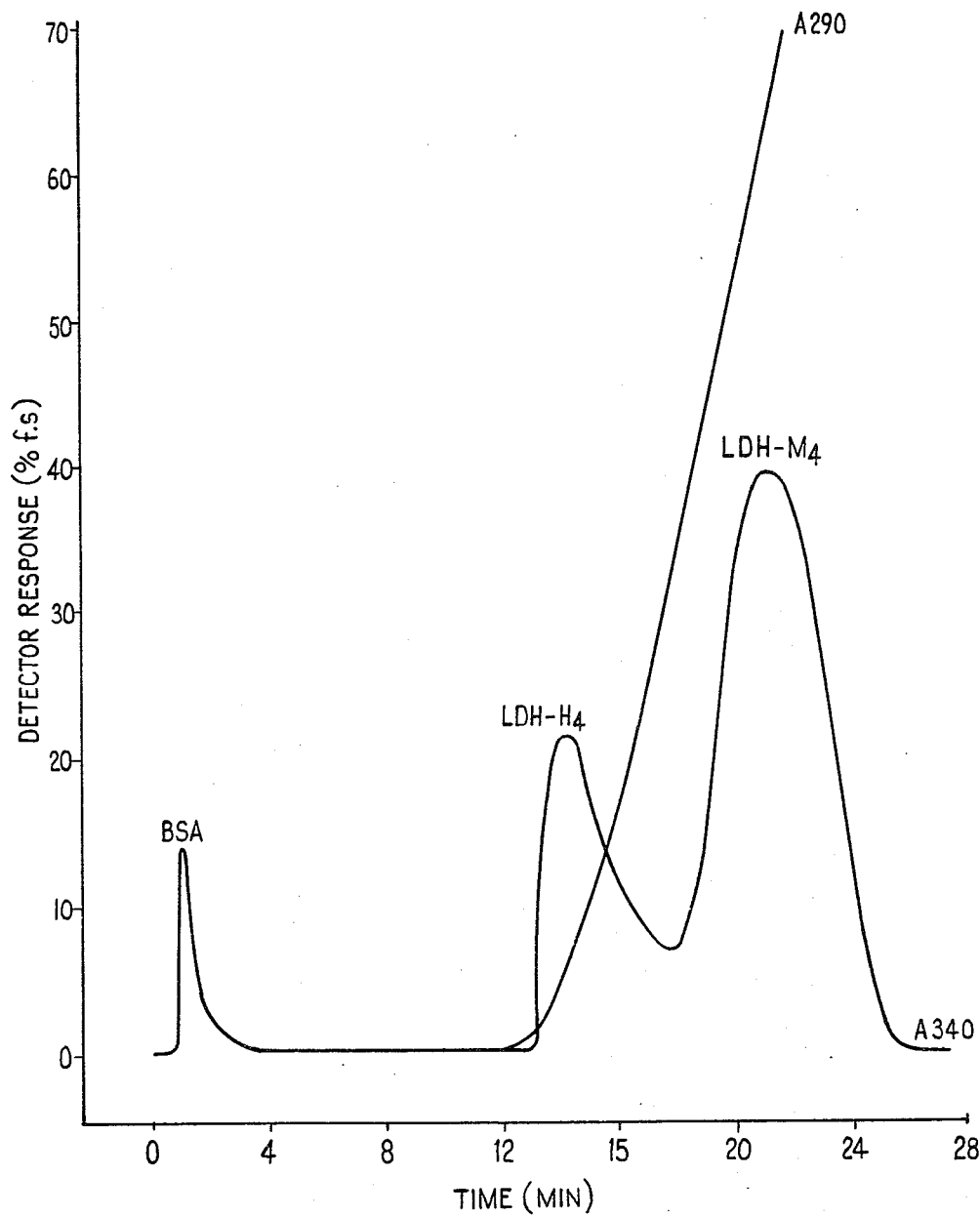

The process and materials of the present invention will now be described by way of example only, with reference to the accompanying drawings in which, FIG. 1 shows, in flow diagrammatic form, an apparatus for the automatic on line detection of lactate dehydrogenase isoenzymes by NADH gradient elution from Cibacron Blue F3G-A/amino-hexylsilica binding material; and FIG. 2 shows, the UV detector response (% f.s at 290 nm and 340nm) against time as lactate dehydrogenase isoenzymes (and bovine serum albumin) are eluted from Cibacron Blue F3G-A/aminohexylsilica by an NADH gradient.

PURIFICATION AND LIGAND PRECURSORS

The ligand precursors employed were triazinyl dyes. Triazinyl dyes were subjected in some cases to an initial purification by precipitating the dye from a methanolic solution with acetone. The dyes were then purified to homogeneity by column chromatography either on Sephadox LH20 (Trade Mark) using 60% aqueous methanol as the eluting solvent or on silica gel using the solvent system isopropanol: amyl alcohol: ethyl acetate: water (40:20:20:20 (v/v/v/v/); or by thin layer chromatography on silica gel using the solvent system isobutanol: n-propanol: ethyl acetate: water (20:40:10:30 (v/v/v/v/).

PREPARATION OF BINDING MATERIALS FOR HPLAC

Example 1

Cibacron Blue F3G-A (Trade Mark) - aminohexyl Silica binding material a. (i) Silica gel (Li-chrosorb Si-60 (Trade Mark), 5 μm, E Merck, 5 g) was suspended in 200 ml of an aqueous solution of γ-glycidoxypropyltrimethoxysilane (1%, pH 5.5; silane Z-6040, Dow Corning). The slurry was treated under reduced pressure in an ultrasonic bath and then heated to and maintained at 90° C. for 2 hr with occasional shaking. The resulting epoxy-silica gel was washed thoroughly with water, dried and could be stored dry without loss of epoxy groups. (ii) Crude Cibacron Blue F3G-A (1.287 g, 60% pure, 1 mmol) was dissolved in 20 ml H$_2$O. 10 ml 1,6-diaminohexane (IM, pH 10.0) was added and the solution was heated at 50° C. for 1 hr. The solution was then added dropwise to 200 ml 0.3 M HCl and incubated for 5 min at 20° C. The precipitate formed was then removed by centrifugation or filtration and thoroughly washed with 0.3 M HCl. The precipitate was then washed with acetone until the supernatant fraction remained colourless and then dried in air to a deep blue powder. The resulting product, 6-aminohexyl-Cibacron F3G-A was more than 90% pure, as measured by tlc on silica (2-butanol: 1-propanol: ethyl acetate water; 20:40:10:30 (v/v/v/v)) and was positive to the 2, 4, 6-trinitrobenzene sulphonic acid test for primary amines. (iii) To 2 g epoxy-silica (step (i) above) was added 10 ml 0.1 M NaHCO$_3$-Na$_2$CO$_3$ (pH 8.6)and 180 mg. 6-aminohexyl-Cibacron Blue F3G-A (step (ii) above), the slurry was sonicated for 10 min under reduced pressure and then incubated overnight at 30° C. with gentle agitation. The Cibacron Blue F3G-A - aminohexyl silica binding material was washed with water (250 ml), IMKCI (250 ml) 50% (v/v) aqueous methanol (200 ml), methanol (200 ml) and ether (100 ml) prior to drying in air to a blue powder.

b. Determination of Bound Dye Concentration

Weighed amounts of dry Cibacron Blue F3G-A-aminohexyl silica (16-60 mg) were added to 5 ml IM-NaOH and heated to 60° C. for 30 min to solubilise the gel. The resulting solution was diluted to approx 25 ml with water, and then the pH was adjusted to 7 with IMHCI. 5 ml IM potassium phosphate buffer pH 7.5 was added, after the solution had been made up to 50 ml with water the absorbance at 620 nm was noted. The immobilised dye concentration, typically 5.5 to 6.7 μmol Cibacron Blue F3G-A/gm dry weight silica, was calculated using a molar extinction coefficient (Em) of 13,600 1/mol/cm for Cibacron Blue F3G-A at 620 nm.

Example 2

Procion Blue MXR (Trade Mark) -aminohexyl Silica Binding Material (i) Procion Blue MXR was purified by one of the procedures outlined above. The purified Procion Blue MXR was then added to an excess of aqueous ammonia and was allowed to react for 15 mins at 15° C. The reaction mixture was then added dropwise to 500 ml of 0.3 MHCI. The precipitated monoamino dye was removed by centrifugation at 3000 rpm for 15 min, washed once with 0.3 MHCI, resuspended in methanol and precipitated with acetone. The dye was then washed with ether and dried. The monoamino Procion Blue MXR was then added to 30 ml IM 1,6-diaminohexane and heated at 50° C. for 2 hours. On completion of the reaction the aminohexyl substituted dye was precipitated by adding the reaction mixture dropwise to 500 ml of 0.3 MHCI. The precipitated dye was removed by centrifugation at 3000 rpm for 15 min, washed once with 0.3 MHCI, resuspended in methanol and precipitated with acetone. Finally the dye was washed with ether and dried in vacuo.

(ii) Epoxy-silica was prepared as outlined above under 1a.(i).

(iii) To 2 g epoxy-silica (step (ii) above) was added 10 ml NaHCO$_3$-Na$_2$CO$_3$ (pH 8.6) and 160 mg. 2-amino-4-aminohexyl-substituted Procion Blue MXR (step (i) above), the slurry was sonicated for 10 min under reduced pressure and then incubated overnight at 30° C. with gentle agitation. The Procion Blue MXR-aminohexyl silica binding material was washed with water (150 ml), IM KCI (250 ml), water (250 ml), 50% (v/v) aqueous methanol (200 ml), methanol (200 ml) and ether (100 ml ) prior to drying in air.

Example 3

Cibacron Blue F3G-A (Trade Mark) - thiopropyl Silica binding material (i) Thiopropyl silica was prepared by the process of Example 1(a)(i) except that γ-mercaptopropyltriethoxysilane replaced γ-glycidoxypropyltrimethoxysilane (ii) To thiopropylsilica (prepared as in 3(i) above, 2 g dry weight) in 0.1 M NaHCO$_3$-Na$_2$CO$_3$ buffer (pH 9.6, 10 ml) was added purified Cibacron Blue F3G-A (81.6 mg). The slurry was sonicated for 10 min and then incubated overnight at 30° C. with gentle agitation. The slurry was washed consecutively with water (250 ml), IM KCI (250 ml), water (1 liter), 50% (v/v) aqueous methanol (200 ml), 100% methanol (200 ml) and ether (100 ml). The derivativised silica was air dried to yield a blue gel containing approx 12.8 μmol Cibacron Blue F3G-A per gram dry weight silica.

Chromatographic procedure

A. The binding material (1.2 g) was packed in polished '316' stainless steel columns (100 mm × 5 mm ID, total volume 2.0 ml) using the upward slurry packing technique of P A Bristow et al, *J Chromatogr*, 1977, 131,57. All chromatographic procedures were performed at ambient temperatures (20°-22° C.).

The pumping system comprised an Altex Model 110A solvent metering pump (Altex, Calif., USA) equipped with a pulse dampener. Ultraviolet detection was performed with a variable wavelength detector, 190-700 nm (LC-55, Perkin Elmer) and sample injections were made with a valve injector (Valco, Houston)

Enzymes eluted from the HPLAC column were detected with an on-line detector system (S H Chang et al, *J Chromatogr,* 1976, 125, 103) comprising a reagent pump (Altex Model 110A); post column reactor, equilibrated to 40° C. in a water bath, and a UV/visible monitor (LC-55, Perkin Elmer). The post column reactor comprised a polished stainless steel '316' column (100 mm×5 mm ID, total volume 2.0 ml) containing non-porous glass beads (150 um) silanised as described by M Glad et al, *J Chromatogr,* 1980,200, 254 with the resulting epoxy groups hydrolysed to diols by heating the 10 mM HCl at 75° C. for 30 min.

B. The binding material was packed into 100 mm×5 mm stainless steel columns by the downward slurry packing technique using a Magnus Scientific Slurry packing unit. 1.5 gm of binding material was suspended in 25 ml methanol and packed into the column at a pressure of 2000 psi. The packing pressure was slowly increased to 3000 psi and this pressure was maintained until 150 ml of solvent had been collected. The solvent was then changed to double distilled water (degassed and filtered through a 0.45μ Millipore filter) and a further 150 ml of solvent was collected. The packed column was detached from the apparatus and a stainless steel sinter was fitted to each end.

When not in use the columns were sealed at both ends with plastic plugs and stored at 15° C.

Assay procedures

The assay solution for the on-line detection of lactate dehydrogenase comprised either 0.4 M Tris-HCl pH 8.8 containing 0.75 M DL-lactate and 1 mM NAD+ or 0.1 M potassium phosphate buffer pH 7.5 containing 1 mM sodium pyruvate and 0.32 mM NADH. The post-column reagent for the detection of liver alcohol dehydrogenase comprised Tris-HCl pH 8.8 (0.4 M) containing ethanol (0.43 M) and NAD+ (1 mM) whilst the reagent for malate dehydrogenase contained potassium phosphate buffer pH 7.5 (0.1 M), oxaloacetate (0.20 mM), and NADH (0.32 nM), and the reagent for *Leuconostoc mesenteroides* glucose-6-phosphate dehydrogenase contained potassium phosphate buffer pH 7.5 (0.1 M), D-glucose-6-phosphate (1.2 mM) and NADP+ (0.4 mM). The assay solution for the simultaneous detection of hexokinase and 3-phosphoglycerate kinase in column effluents was prepared in Triethanolamine-HCl pH 8.0 (0.1 M) and contained ATP (0.41 mM), NADP+ (0.31 mM), NADH (48 μm), D-glucose (0.125 M), 3-phosphoglycerate (5.0 mM), glucose-6-phosphate dehydrogenase (1.25 μg/ml; 0.5 μ/ml) and glyceraldehyde-3-phosphate dehydrogenase (38.6 μg/ml; 2.7 (μ/ml). In each case enzyme activity was monitored by the change in absorbance at 340 nm.

Bovine pancreatic Ribonuclease A activity was monitored by the decrease in absorbance at 305 nm following hydrolysis of RNA to oligonucleotides. The assay solution contained RNA (2.2 mg/ml) in sodium acetate buffer pH 5.0 (0.1 M). Alkaline phosphatase activity was monitored at 410 nm with assay medium comprising p-nitrophenylphosphate (disodium salt) (4 mM) in tris-HCl pH 8.0 (0.25 M).

Yeast Hexokinase activity was followed spectrophotometrically (at 340 nm) by an assay procedure which employed the coupled reduction of NADP+ with glucose-6-phosphate dehydrogenase. The reaction mixture (1 ml) contained:

| | |
|---|---|
| Tris HCl (pH 7.5) | 30 μMole |
| D-glucose | 5 μMole |
| ATP | 3 μMole |
| NADP+ | 0.7 μMole |
| magnesium chloride | 10 μMole |
| Yeast glucose-6-phosphate dehydrogenase | 3 units |

1 unit of yeast hexokinase is defined as the amount required to produce 1 μMole of NADPH per min at 30° C. (for details of an assay see P B Garland et al, *Nature,* 1962, 196,987).

The assay for calf intestine alkaline phosphatase, which was performed at 30° C., employed an aqueous reaction mixture, with a total volume of 1 ml., and containing:

| | |
|---|---|
| Glycine buffer (pH 10.5) | 100 μMole |
| magnesium chloride | 1 μMole |
| Zinc chloride | 0.1 μMole |
| p-nitrophenol phosphate | 6 μMole |

1 unit of phosphatase activity is defined as the amount of enzyme required to produce 1 μMole of p-nitrophenol per min at 30° C. (For details of this assay see O A Bessey et al, *J Biol Chem* 1946, 164, 321).

The assay for Carboxypeptidase, which was performed at 37° C., employed an aqueous reaction mixture, with a total volume of 1 ml, and containing:

| | |
|---|---|
| 100 μMole | Tris-HCl (pH 7.3) |
| 60 μMole | methotrexate |
| 200 nMole | Zinc chloride and |
| 10 μl | enzyme solution eluted from the column (0.1 to 1 unit of enzyme) |

Enzyme activity was measured by determining the decrease in a absorbance of the solution at 320 nm (for details of this assay see J L McCulloch et al, *J Biol Chem.,* 1971, 246, 7207).

On line detection of protein (280 nm) and enzyme activity (305, 320, 340 or 410 nm respectively) was continuously displayed on a two channel record (Omniscribe 3500, Houston Instruments, Texas USA).

SEPARATION OF BIOLOGICAL SUBSTANCES BY HPLAC

Example 4

Separation of Pig heart lactate dehydrogenase (LDH-H$_4$) and Bovine serum albumin (BSA)

Column:
Cibacron Blue F3G-A/aminohexylsilica binding material (Example 1; 6.6 μmol dye/gm silica), packing onto a column by the above chromatographic procedure Sample:
LDH-H$_4$ (0.1 mg/ml) and BSA (0.6 mg/ml) in 0.1 M potassium phosphate buffer (pH 7.5)

Sample volume
50 μl

Column washing solution:
0.1 M potassium phosphate (pH 7.5)

Column eluting solution:
15.75 mM NAD+ in. 0.1 M potassium phosphate buffer (pH 7.5)

Flow rate:

1 ml/min at both sample and reagent pumps
Pressure:
1200 psi (sample pump); 200 psi (reagent pump)
Assay for on line detection:
0.4 M Tris-HCl buffer (pH 8.8) containing 0.75 M D, L-lactate and and 1 mM NAD+
Detector wavelengths:
280 nm (protein), 340 nm (NADH, enzyme activity)

Example 5

Separation of Horse Liver Alcohol dehydrogenase (LADH) and Bovine serum albumin (BSA)

Column:
as Example 4
Sample:
LADH (0.2 mg/ml) and BSA (0.6 mg/ml) in 0.1 M potassium phosphate buffer (pH 7.5)
Sample volume:
as Example 4
Washing solution:
as Example 4
Eluting solution:
0.1 mM pyrazole and 1 mM NAD+ in 0.1 M potassium phosphate buffer (pH 7.5)
Flow rate:
as Example 4
Pressures:
as Example 4
Assay for on line detection:
0.4 M Tris-HCl (pH 8.8) containing 0.43 M EtOH and 1 mM NAD+.
Detector wavelengths:
280 nm (protein), 340 nm (NADH enzyme activity)

Example 6

Separation of pig heart lactate dehydrogenase (LDH-$H_4$) horse liver alcohol dehydrogenase(LADH) and bovine serum albumin (BSA)

Column:
as Example 4
Sample:
LDH-$H_4$ (0.1 mg/ml), LADH (0.2 mg/ml) and BSA (0.6 mg/ml) in 0.1 M potassium phosphate buffer (pH 7.5)
Sample volume:
as Example 4
Washing solution:
as Example 4
Eluting solutions: (add sequentially)
a. 1 mM NAD+
b. 1 mM NAD+/0.1 mM pyrazole;
c. 1 mM NAD+/0.1 mM pyruvate all in 0.1 M potassium phosphate buffer (pH 7.5)
Flow rate:
as Example 4
Pressures:
as Example 4
Assay for on line detection
a. LADH - 0.4 M Tris HCl (pH 8.8) containing 0.43 M EtOH and 1 mM $NAD^{30}$
b. LDH - 0.4 M Tris HCl (pH 8.8) containing 0.75 M D, L-lactate and 1 mM NAD+
Detector wavelengths:
280 nm (protein), 340 nm (NADH, enzyme activity).

Example 7

Separation of Leuconostoc mesenteroides glucose-6-phosphate dehydrogenase (GPD) and Bovine serum albumin (BSA)

Column:
as Example 4
Sample:
GPD (0.026 mg/ml) and BSA (0.6 mg/ml) in 0.1 M potassium phosphate buffer (pH 7.5)
Sample volume
100 μl
Washing solution:
as Example 4
Eluting solution
4.2 mM NADP+ in 0.1 M potassium phosphate (pH 7.5)
Flow rate:
as Example 4
Pressures:
as Example 4
Assay for on line detection:
0.1 M potassium phosphate buffer (pH 7.5) containing 1.2 mM glucose-6-phosphate and 0.4 mM NADP+
Detector wavelengths:
280 mm (protein,) 340 mm (NADH, enzyme activity

Example 8

Separation of pig heart lactate dehydrogenase (LDH-$H_4$) rabbit muscle lactate dehydrogenase (LDH-$M_4$) and bovine serum albumin (BSA)

Column:
as Example 4
Sample:
LDH-$H_4$ (0.065 mg/ml), LDH-$M_4$ (0.59 mg/ml) and BSA (3 mg/ml) in 0.1 M potassium phosphate (pH 7.5)
Sample Volume:
20 μl
Washing solution:
as Example 4
Eluting solution:
an increasing gradient of NADH (conc OmM) to 4 mM) in 0.1 M potassium phosphate buffer (pH 7.5); 20 ml mixing volume
Flow rate:
as Example 4
Pressures:
1000 psi (sample pump), 200 psi (reagent pump)
Assay for on line detection
1 mM sodium pyruvate, 0.32 mM NADH in 0.1 M phosphate buffer (pH 7.5)
Detector wavelength:
290 nm (protein), 340 nm (NADH, isoenzyme activity).

The resolution of LDH-$H_4$, LDH-$M_4$ and BSA is effected with continuous on-line monitoring of protein concentration, gradient profile and isoenzyme activity.

FIG. 1 illustrates the experimental set-up required for automatic recording of the entire chromatographic profile shortly after the last isoenzyme peak has emerged from the analytical column. The system automatically corrects for the increased absorbance in the post-column enzyme detector due to the NADH gradient.

The automatic recording apparatus illustrated in FIG. 1 comprises a gradient maker (1) which provides an increasing NADH(E)gradient to a first pump (2). The pump (2) pumps the eluting solution through an injection valve (3) and an HPLAC column (4). The effluent flow from the HPLAC column (4) is passed through a UV-detector (5) set at 290 nm to monitor protein in the void volume and, subsequently, the gradient profile due to absorbance of NADH($\epsilon$ 1,400 1/mol/cm at 290 mm) before being split equally at a T-piece (6). One half of the split flow passes on to the post column reactor (7) where, immediately prior to the column (7), it is mixed with half of the split flow from the reagent pump (8). The effluent from the post column reactor (7) flows directly through the sample cuvette of the enzyme activity detector (9) set at 340 nm. The other half of the flow of assay mixture from the reagent pump (8) is mixed with the effluent from the UV detector (5), by-passes the post column reactor (7) and passes through the reference cuvette of the enzyme activity detector (9).

Thus, when no enzyme activity is eluted from the analytical HPLAC column (4), the system is fully compensated irrespective of the NADH gradient profile and zero absorbance is recorded on the enzyme activity monitor (9). By contrast, eluted isoenzymes in the flow from the post column reactor (7) reduce the absorbance in the sample cuvette and produce positive peaks on a 2-channel recorder (10) when the polarity of the signal is reversed.

FIG. 2 illustrates a typical fully automated chromatographic profile representing the NADH gradient elution of BSA, LDH-$H_4$ and LDH-$M_4$ under the conditions of the present Example.

Example 9

Separation of ribonuclease A from crude bovine pancreatic extract

Column:
  as Example 4
Sample:
  Crude bovine pancreatic extract containing crystalline ribonuclease A (10 mg/ml)
Sample volume:
  50 $\mu$l
Column washing solution:
  10 mM sodium acetate (pH 5.0)
Column eluting solution:
  10 mM Cytidine 2-monophosphate disodium salt (50 $\mu$L)
Flow rate:
  1 ml/min (sample pump), 2 ml/min (reagent pump)
Pressures:
  as Example 4
Assay for on line detection
  RNA (2.2 mg/ml) in 0.1 M sodium acetate (pH 5.0)
Detector wavelengths:
  280 nm (protein), 305 nm (enzyme activity)

Example 10 (HPLAC using metal ions)

The use of metal ions in the chromatographic separation of biological substances is described in our co pending UK patent application no 8112925 (Agents Ref: JX/5964/02)

A. Preparation of Binding Material (i) Silica gel (Li-chrosorb Si-60 (Trade Mark), 5 $\mu$m, 5 g, E Merck) was suspended in 200 ml of an aqueous solution of $\gamma$-glycidoxypropyltrimethoxysilane (1%, pH 5.5; silane Z - 6040, Dow Corning). The slurry was treated under reduced pressure in an ultrasonic bath and then heated to and maintained at 90° C. for 2 hr. with occasional shaking. The resulting epoxy-silica gel was washed thoroughly with water, dried and could be stored dry without loss of epoxy groups.

(ii) Crude Procion Green H4G (1 mM) was dissolved in 20 ml $H_2O$. 10 ml of 1,6-diamino hexane (1M, pH 10.0) was added and the solution was heated at 50° C. for 1 hr. The solution was then added dropwise to 200 ml 0.3 M HCl and incubated for 5 min at 20° C.

The precipitate formed was then removed by centrifugation or filtration and thoroughly washed with 0.3 M HCl. The precipitate was then washed with acetone until the supernatant fraction remained colourless and then dried in air to a deep green powder. The resulting product, 6-aminohexyl - Procion Green H4G was more than 90% pure, as measured by tlc on silica (2 -butanol: 1 -propanol: ethyl acetate: 20:40:10:30 (v/v/v/v)) and was positive to the 2, 4, 6-trinitrobenzene sulphonic acid test for primary amines.

(iii) To 2 g epoxy -silica (step (i) above) was added 10 ml. 0.1 M $NaHCO_3$- $Na_2CO_3$(pH 8.6) and 180 mg 6-aminohexyl-Procion Green H4G (step (ii) above), the slurry was sonicated for 10 min under reduced pressure and then incubated overnight at 30° C. with gentle agitation.

The Procion Green H4G - aminohexyl - epoxysilica binding material was washed with water (250 ml), 50% (v/v) aqueous methanol (200 ml), methanol (200 ml) and ether (100 ml) prior to drying in air to a green powder.

B. Chromatographic procedure (i) The binding material (1.2 g) was packed in polished '316' stainless steel columns (100 mm × 5 mm; I D, total volume 2.0 ml) using the upward slurry packing technique of P. A. Bristow et al, *J Chromatogr.*, 1977, 131, 57. All chromatographic procedures were performed at ambient temperature (20°–22° C.). The pumping system comprised an Altex Model 110A solvent metering pump (Altex, Calif., USA) equipped with a pulse dampener. Ultraviolet detection was performed with a variable wavelength detector, 190–700 nm (LC -55, Perkin Elmer) and sample injections were made with a valve injector (Valco, Houston). Enzymes eluted from the High Pressure Liquid Affinity Chromatography (HPLAC) column were detected with an on-line detector system (S. H. Chang et al, *J Chromatogr.*, 1976, 125, 103) comprising a reagent pump (Altex Model 110A), post column reactor, equilibrated to 40° C. in a water bath, and a UV/visible monitor (LC - 55, Perking Elmer). The post column reactor comprised a polished stainless steel '316' column (100 mm × 5 mm; I.D., total volume, 2.0 ml) containing non porous glass beads (150 $\mu$m) silanised as described by M Glad et al *J Chromatogr.*, 1980, 200, 254 with the resulting epoxy groups hydrolysed to diols by heating in 10 mM HCl at 75° C. for 30 min.

(ii) The binding material was packed into 100 mm × 5 mm stainless steel columns by the downward slurry packing technique using a Magnus Scientific slurry packing unit. 1.5 gm of binding material was suspended in 25 ml methanol and packed into the column at a pressure of 2000 psi. The packing pressure was slowly increased to 3000 psi and this pressure was maintained until 150 ml of solvent had been collected. The solvent was then changed to double distilled water (degassed and filtered through a 0.45μ Millipore filter) and a further 150 ml of solvent was collected. The packed column was detached from the apparatus and a stainless steel sinter was fitted to each end.

When not in use the column were sealed at both ends with plastic plugs and stored at 15° C.

Separation of Yeast Hexokinase

The column was packed with Procion Green H4G - aminohexyl-epoxysilica binding material by the method described above (10B). It was then equilibrated, at a sample pump pressure of 1200 psi - reagent pump pressure of 200 psi and a flow rate of 1 ml/min, with 10 mM HEPES buffer (pH 7.5). The contact solution (0.1 ml), made up of yeast hexokinase (0.2 mg/ml), 10 iu/mg) and magnesium chloride (to 10 mM) dissolved in 10 mM HEPES buffer (pH 7.5), was then loaded onto the column under pressure (sample pump 1200 psi, reagent pump 200 psi). A further 1 ml aliquot of the contact solution, but without the enzyme, was then passed down the column under the same pressure, to remove any non-binding species from the column. Using the assay procedure described above the % (by activity) of yeast hexokinase that was retained on the column was determined. This was found to be 90% of enzyme activity. Finally the enzyme was recovered from the column by either:
 a. Applying a pulse (0.2 ml) of 0.5 M KCl, or
 b. Applying a pulse (0.2 ml) of 2 mM and 1 mM Mg.

Example 11

Separation of Carboxypeptidase G by HPLAC

The procedure of Example 10 was repeated except that Yeast hexokinase was replaced by Carboxypeptidase G as the enzyme, Procion Green H4G was replaced by Procion Yellow HA as the dye and magnesium chloride (10 mM) was replaced by zinc chloride (0.2 mM) as the source of metal ions. Using the assay procedure described above the % (by activity) of Carboxypeptidase G that was retained on the column was determined. This was found to be 100% of enzyme activity.

Finally the enzyme was recovered from the column by applying a pulse (0.2 ml) of 0.2 M KCl.

Example 12

A. Procion Yellow HA - aminohexyl - epoxysilica binding material was prepared as in Example 11

B. Separation of Calf Intestine Alkaline Phosphatase i. The HPLAC procedure of Example 11 was repeated except that alkaline phosphatase replaced carboxypeptidase G as the enzyme. Using the assay procedure described above the % (by activity) of alkaline phosphatase that was retained on the column was determined. This was found to be 0%.

ii. The HPLAC procedure of Example 11 was repeated except that, before the contact solution was loaded onto the column, the binding material was treated with a 0.2 mM solution of zinc chloride. Under these conditions 100% (by activity) of enzyme was retained on the column. Finally the enzyme was recovered from the column by applying a pulse (0.2 ml) of 0.2 M KCl.

Example 13

A. Preparation of Binding Material for HPLAC i. Silica gel (Li-chrosorb Si - 60 (Trade Mark), 5 μm, E. Merck, 5 g.) was suspended in 200 ml of an aqueous solution of γ-glycidoxypropyltrimethoxysilane (1%, pH 5.5-, silane Z - 6040, Dow Corning). The slurry was treated under vacuum in an ultrasonic bath and was then heated to and maintained at 90° C. for 2 hr. with occasional shaking. The solution was then cooled and the pH was adjusted to 3.5. Further heating at 90° C. for 1 hr. converted the oxirane groups of the gel to glycol groups.

ii. To 2 g. glycol-silica (step i. above) was added 10 ml. 0.1 M $NaHCO_3$-$Na_2CO_3$ (pH 8.6) and 160 mg. Procion Brown MX -5BR. The slurry was sonicated for 10 min. under reduced pressure and then incubated overnight at 30° C. with gentle agitation. The Procion Brown MX - 5 BR - glycol silylated silica binding material was washed with water (250 ml.), 1 M KCl (250 ml.), 50% (v/v) aqueous methanol (200 ml.), methanol (200 ml.) and ether (100 ml.) prior to drying in air to a brown powder.

B. Separation of Tryptophanyl - tRNA synthetase

Column:
 Procion Brown MX - 5 BR/glycol silylated silica binding material (Example 13 A) packing onto a column by the above chromatographic procedure
Sample:
 Tryptophanyl -tRNA synthetase (1 mg/ml) in 10 mM HEPES buffer (pH 7.0).
Sample volume:
 20 μl
Column washing solution:
 10 mM HEPES buffer (pH 7.0)
Column eluting solution:
 10 mM ATP (200 μl) or 0.5 M KCl (200 μl).
Flow rate:
 2 ml/min at both sample and reagent pumps.
Pressure:
 500 psi (3.5 M Pa) at sample pump; 200 psi at reagent pump.
Assay for synthetase detection:
 as described by R. L. Heinrikson et al, *Biochem J.*, 1967, 105, 17.
Detector wavelengths:
 280 nm (protein), 340 nm (NADH, enzyme activity.)

Example 14

A. Preparation of Binding Material for HPLAC

Procion Blue MXR - glycol silylated silica binding material was prepared as described in Example 13A except that Procion Blue MXR replaced Procion Brown MX - 5BR as the dye.

B. Separation of pig heart lactate dehydrogenase LDH-$H_4$) and bovine serum albumin (BSA)

Column:
 Procion Blue MXR - glycol silylated silica binding material (Example 14A) packed onto a column by the above chromatographic procedure.
Sample:
 A mixture of BSA (10 μg) and LDH-$H_4$ (10 μg) in 10 mM HEPES buffer (pH 7).
Sample volume:
 20 μl Column washing solution:
 10 mM HEPES buffer (pH 7)
Column eluting solution:
 (a) 0.5 M KCl in 10 mM HEPES buffer (pH 7) (200 μl), or
 (b) 0.1 mM NAD+/0.1 M Pyruvate in 10 mM HEPES (pH 7) (200 μl).
Flow rate:
 1 ml/min at both sample and reagent pumps
Pressure: 500 psi (3.5 MPa) at sample and reagent pump;
LDH assay:
 1 mM sodium pyruvate, 0.32 mM NADH in 0.1 M phosphate buffer (pH 7.5).
Detector wavelength:
 280 nm.

Example 15

Purification of crude rabbit muscle lactate dehydrogenase (LDH-M₄)

Column:
 as Example 14 (0.46 cm × 10 cm).
Sample:
 LDH/M₄ (200 μg) in 25 mM potassium phosphate buffer (pH 7) or 10 mM HEPES buffer (pH 7)
Sample volume:
 20 μl
Column washing solution:
 25 mM potassium phosphate buffer (pH 7) or 10 mM HEPES buffer (pH 7)
Column eluting solution:
 0.5 M KCl in 10 mM HEPES buffer (pH 7)
Flow rate:
 1 ml/min at both sample and reagent pumps.
Pressure:
 100 psi (0.69 MPa) at sample and reagent pumps
LDH assay:
 1 mM sodium pyruvate 0.32 mM NADH in 0.1 M phosphate buffer (pH 7.5).
Detector wavelength:
 280 nm.

Example 16

Large scale purification of crude rabbit muscle lactate dehydrogenase (LDH-M₄)

Column:
 as Example 14 (2.5 cm × 30 cm)
sample:
 LDH-M₄ (100 mg, 130 u/mg) and BSA (100 mg) in 10 mM HEPES (pH 7.0)
Sample volume:
 100 ml.
Column washing solution :
 10 mM HEPES buffer (pH 7.0)
Column eluting solution:
 0.5 M KCl in 10 mM HEPES buffer (pH 7)
Flow rate:
 5 ml/min at both sample and reagent pumps
Pressure:
 500 psi (3.5 MPa) at sample and reagent pumps
LDH assay:
 1 mM sodium pyruvate, 0.32 mM NADH in 0.1 M phosphate buffer (pH 7.5), assays are done manually
Detector wavelength:
 280 nm.

What I claim is:

1. A process for the high pressure liquid affinity chromatographic separation of at least one biological substance from a mixture containing same comprising the steps of (a) contacting the mixture containing the at least one biological substance with a binding material retained on a chromatographic column to bind the biological substance to the binding material, (b) passing a washing solution through the binding material to remove non-binding species from the column, and (c) passing an eluting solution through the binding material to recover the at least one biological substance from the column, the improvement which comprises performing at least the steps (a) and (b) at a pressure of between 10 and 5000 psi on a binding material of general formula

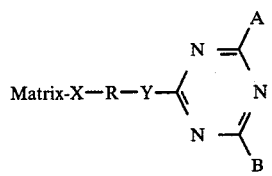

wherein the matrix is an affinity chromatographic support, compatible with a pressure of between 10 and 5000 psi, selected from alumina, titania, zirconia, silica and glass beads, X—Y—R is a spacer arm wherein X is

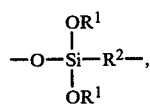

$R^1$ is selected from H and alkyl, $R^2$ is at least one group selected from alkyl, substituted alkyl, diol, ether, amido and amino, R is at least one group selected from alkyl, alkene, -aminoalkyl, -oxyalkyl, -thioalkyl, alkyl alcohol, diol, carboxylate, ether, thioether, amido, amino, amidino, imino carboxylate, isourea, carbamate, quanidino, hydrazino, aromatic and heterocyclic groups, Y is selected from alkyl, ether, thioether, amido, amino, —NH—, —O— and —S—, A is an organic substituent containing a group selected from anthraquinone, aromatic azo and phthalocyanine and B is selected from an organic substituent, a halogen atom, an amino group and a substituted amino group said binding material being so constructed that the at least one biological substance is retained on the binding material during steps (a) and (b) of the process.

2. A process according to claim 1 wherein A is a sulphonated anthraquinone.

3. A process according to claim 1 wherein B is a sulphonated aromatic group.

4. A process according to claim 1 wherein B is a chlorine atom.

5. A process according to claim 1 wherein the matrix is silica, X is

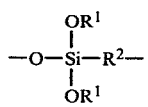

wherein $R^1$ is selected from the group consisting of H and alkyl, $R^2$ is at least one group selected from the group consisting of alkyl, substituted alkyl, diol, ether, amido and amino, R is at least one group selected from the group consisting of alkyl, alkene, α-aminoalkyl, α-oxyalkyl, α-thioalkyl, alkyl alcohol, diol, carboxylate, ether, thioether, amido, amino, amidino, imino carboxylate, isourea, carbamate, guanidino, hydrazino, aromatic and heterocyclic groups and Y is selected from the group consisting of alkyl, ether, thioether, amido, amino, —NH—, —O— and —S—.

6. A process according to claim 5 wherein $R^2$ is at least one group selected from the group consisting of alkyl, substituted alkyl and alkyl ether, R is selected from the group consisting of —(CH$_2$)$_n$, —NH(CH$_2$)$_n$, —O(CH$_2$)$_n$, —S(CH$_2$)$_n$ wherein n is from 1 to 12, polyethyleneimine, polylysine, polyarginine, polyvinylpyrrolidone, polyornithine, polyvinylamine and a phenyl derivative and Y is selected from the group consisting of —NH—, —O— and —S—.

7. A process according to claim 6 wherein R is selected from the group consisting of —(CH$_2$)$_n$, —NH(CH$_2$)$_n$, —O(CH$_2$)$_n$, and —S(CH$_2$)$_n$, wherein n is from 1 to 12.

8. A process according to claim 7 wherein —X—R—Y— is selected from the group consisting of —OSi(OR$^1$)$_2$(CH$_2$)$_3$O CH$_2$ CH(OH)CH$_2$ NH(CH$_2$)$_6$ NH—, —OSi(OR$^1$)$_2$ CH$_2$ CH$_2$ CH$_2$ S— and —OSi(OR$^1$)$_2$ (CH$_2$)$_3$O CH$_2$ CH(OH)CH$_2$O—.

9. A processs according to claim 1 wherein the at least one biological substance is selected from the group consisting of an enzyme, a polypeptide and a protein.

10. A process according to claim 9 wherein the at least one biological substance is selected from the group consisting of an albumin, a peptidase, a phosphatase, a kinase, a nuclease, a dehydrogenase, an esterase, a synthetase, a DNA binding protein and a RNA binding protein.

11. A binding material for use in a process according to claim 1 for the high pressure liquid affinity chromatographic separation of at least one biological substance from a mixture containing same, said process comprising the steps of
(a) contacting the mixture containing the at least one biological substance with the binding material retained on a chromatographic column to bind the biological substance to the binding material,
(b) passing a washing solution through the binding material to remove non-binding species from the column, and
(c) passing an eluting solution through the binding material to recover the at least one biological substance from the column, wherein the binding material is of general formula

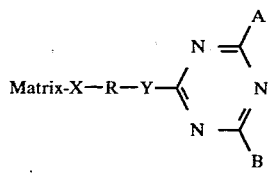

wherein the matrix is an affinity chromatographic support, compatible with a pressure of between 10 and 5000 psi, selected from alumina, titania, zirconia, silica and glass beads, X—Y—R is a spacer arm wherein X is

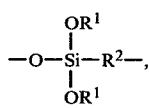

$R^1$ is selected from H and alkyl, $R^2$ is at least one group selected from alkyl, substituted alkyl, diol, ether, amido and amino, R is at least one group selected from alkyl, alkene, -aminoalkyl, -oxyalkyl, -thioalkyl, alkyl alcohol, diol, carboxylate, ether, thioether, amido, amino, amidino, imino carboxylate, isourea, carbamate, guanidino, hydrazino, aromatic and heterocyclic groups, Y is selected from alkyl, ether, thioether, amido, amino, —NH—, —O— and —S—, A is an organic substituent containing a group selected from anthraquinone, aromatic azo and phthalocyanine and B is selected from an organic substituent, a halogen atom, an amino group and a substituted amino group and is so constructed that the at least one biological substance is retained on the binding material during steps (a) and (b) of the process.

12. A binding material according to claim 11 wherein the matrix is silica, X is

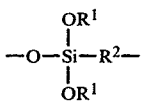

wherein $R^1$ is selected from the group consisting of H and alkyl, and $R^2$ is at least one group selected from the group consisting of alkyl, substituted alkyl and alkyl ether, R is selected from the group consisting of —(CH$_2$)—$_n$, —NH(CH$_2$)—$_n$, —O(CH$_2$)—$_n$ and —S(CH$_2$)—$_n$, wherein n is from 1 to 12 and Y is selected from the group consisting of —NH—, —O— and —S—.

13. A process for the preparation of a binding material according to claim 12 wherein
R is —NH (CH$_2$)$_n$— and Y is —NH— comprising:
(a) reacting a silica matrix with a w-glycidoxyalkyltrialkoxysilane to form a modified matrix,
(b) reacting a monochloro triazine dye with an, w-diaminoalkane to form a modified dye, and
(c) reacting the modified matrix with the modified dye to form the binding material.

* * * * *